(12) United States Patent
Orr (10) Patent No.: US 8,672,992 B2
(45) Date of Patent: Mar. 18, 2014

(54) STENT AND STENT-GRAFT HAVING ONE OR MORE CONFORMANCE STRUTS

(75) Inventor: David E. Orr, Central, SC (US)

(73) Assignee: Cook Medical Technologies LLC, Bloomington, IN (US)

( * ) Notice: Subject to any disclaimer, the term of this patent is extended or adjusted under 35 U.S.C. 154(b) by 515 days.

(21) Appl. No.: 12/641,125

(22) Filed: Dec. 17, 2009

(65) Prior Publication Data

US 2010/0161027 A1   Jun. 24, 2010

Related U.S. Application Data

(60) Provisional application No. 61/138,643, filed on Dec. 18, 2008.

(51) Int. Cl.
*A61F 2/06* (2013.01)

(52) U.S. Cl.
USPC ........................................ 623/1.13

(58) Field of Classification Search
USPC ............... 606/108, 198, 194; 623/1.11–1.16, 623/1.35, 1.36, 1.23
See application file for complete search history.

(56) References Cited

U.S. PATENT DOCUMENTS

| | | | |
|---|---|---|---|
| 5,282,824 A | | 2/1994 | Gianturco |
| 6,027,526 A | * | 2/2000 | Limon et al. .................. 623/1.15 |
| 6,379,382 B1 | * | 4/2002 | Yang ............................ 623/1.42 |
| 6,464,723 B1 | * | 10/2002 | Callol .......................... 623/1.34 |
| 6,602,281 B1 | | 8/2003 | Klein |
| 7,175,652 B2 | | 2/2007 | Cook et al. |
| 2003/0070676 A1 | * | 4/2003 | Cooper et al. ........... 128/200.24 |
| 2005/0043752 A1 | * | 2/2005 | Phan et al. ..................... 606/155 |
| 2005/0131519 A1 | | 6/2005 | Hartley |
| 2007/0173929 A1 | | 7/2007 | Boucher et al. |
| 2007/0233229 A1 | | 10/2007 | Berra et al. |
| 2007/0233233 A1 | | 10/2007 | McGovern et al. |
| 2008/0015673 A1 | | 1/2008 | Chuter |
| 2008/0015687 A1 | * | 1/2008 | Lashinski et al. .............. 623/2.1 |
| 2008/0097576 A1 | * | 4/2008 | Cottone et al. ............... 623/1.15 |
| 2008/0132993 A1 | | 6/2008 | Rasmussen et al. |
| 2009/0149946 A1 | * | 6/2009 | Dixon .......................... 623/1.36 |
| 2010/0094405 A1 | * | 4/2010 | Cottone ....................... 623/1.16 |

FOREIGN PATENT DOCUMENTS

WO   WO2006/127784   11/2006

OTHER PUBLICATIONS

On-line information for WallFlex Colonic Stent, Boston Scientific website: http://www.bostonscientific.com/; printed Aug. 20, 2008, page no longer available.
On-line information for FerX-ELLA Esophageal Stent, CS ELLA website, http://www.ellacs.eu/product-detail.php?id=17&category=3 ; printed Aug. 20, 2008.
International Search Report and Written Opinion for PCT/US2009/068201 (16 pgs), Mar. 23, 2010.

* cited by examiner

*Primary Examiner* — Thomas McEvoy
*Assistant Examiner* — Jocelin Tanner
(74) *Attorney, Agent, or Firm* — Brinks Gilson & Lione (57) ABSTRACT

A stent includes a main body having proximal and distal ends, and at least one conformance strut coupled to the proximal end of the main body. A portion of the at least one conformance strut extends proximal to a proximal end of a graft material in a compressed delivery configuration, and further is aligned inside the proximal end of the graft material in an expanded deployed configuration. In the deployed configuration, the proximal conformance strut may at least partially encircle the graft material just distal to the proximal end of the graft material, which may reduce the likelihood of infolding at the proximal edge of the graft material and potential endoleaks.

17 Claims, 6 Drawing Sheets

STENT AND STENT-GRAFT HAVING ONE OR MORE CONFORMANCE STRUTS

PRIORITY CLAIM

This invention claims the benefit of priority of U.S. Provisional Application Ser. No. 61/138,643, entitled "Stent and Stent-Graft Having One or More Conformance Struts," filed Dec. 18, 2008, the disclosure of which is hereby incorporated by reference in its entirety.

BACKGROUND

The present invention relates generally to apparatus and methods for treating medical conditions, and more specifically, to stents and stent-grafts for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents may be used a part of a "stent-graft," whereby one or more stents are placed in or about a graft and used to hold the graft in an open configuration to treat an aneurysm or other condition. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When a stent-graft having at least one stent is deployed in a vessel, such as the aorta, and blood flows in a proximal to distal direction away from the heart, there is a possibility of "infolding" of graft material, particularly at the proximal end of the graft material. For example, if a stent-graft is deployed to treat an abdominal aortic aneurysm, blood flowing distally into the graft may pull the proximal edge of the graft in a radially inward direction, particularly if an optimal proximal seal is not achieved with the vessel wall. In this case, the graft material that becomes pulled inward may impede blood flow through the stent-graft lumen, or an endoleak may occur. Furthermore, if the proximal end of a stent-graft is deployed in a curved portion of a vessel, such as the aortic arch or thoracic aorta, it may be difficult to conform the proximal edge of the stent-graft to the curving vessel wall, which also may result in blood flow catching on the graft and potential endoleaks.

SUMMARY

The present embodiments provide a stent, which may be used alone or as part of a stent-graft to treat a medical condition. In one embodiment of an exemplary stent-graft, at least one stent is coupled to a substantially tubular graft material. A proximal end of the stent comprises at least one conformance strut having a compressed delivery configuration and an expanded deployed configuration.

In the compressed delivery configuration, the at least one conformance strut comprises an outwardly extending loop that is substantially parallel to a longitudinal axis of the stent and extends beyond a proximal end of the graft material. In the deployed configuration, the at least one conformance strut is disposed substantially perpendicular to the longitudinal axis and aligned inside the proximal end of the graft material. Accordingly, in the deployed configuration, the at least one proximal conformance strut may at least partially encircle the graft material just distal to the proximal end of the graft material.

The main body may comprises a zig-zag shape in the deployed configuration comprising a plurality of substantially straight first segments and second segments, and having a plurality of proximal and distal apices disposed between the first segments and second segments. In this embodiment, each of the proximal conformance struts may comprise a first end, a second end, and a central region formed therebetween, where the first end of the conformance strut is coupled to a first proximal apex of the main body, and the second end of the conformance strut is coupled to an adjacent, second proximal apex of the main body.

The at least one conformance strut may be integrally formed with the main body. During delivery, the central region of the conformance strut may comprise an arcuate shape that extends proximal to the proximal end of the graft material. When expanded, the conformance strut may comprise a wave-shaped configuration, or alternatively may comprise convex or concave-shaped configurations relative to the main body.

Advantageously, in the deployed configuration, the proximal conformance struts may at least partially encircle the graft material just distal to the proximal end of the graft material, which may reduce the likelihood that blood flow may catch on the proximal edge of the graft material. Therefore, blood that flows in a distal direction through the stent-graft is less likely to pull the proximal edge of the graft material in a radially inward direction, which may reduce potential endoleaks. Furthermore, the use of a stent, in accordance with the present embodiments, as part of a stent-graft may be well-suited for use in a curved portion of a vessel, such as the thoracic aorta, where it may be difficult to conform the proximal edge of the stent-graft to the curving vessel wall.

Furthermore, the proximal conformance struts do not overlap with the main body of the stent in the compressed delivery configuration, which may allow the stent to be compressed to a relatively small delivery profile, and therefore may be used in smaller vessels or ducts. Still further, a stent-graft according to the present embodiments may find particular use in applications where it may not be desirable to have a bare stent segment extending proximal or distal to the graft material in a deployed configuration.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention.

Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
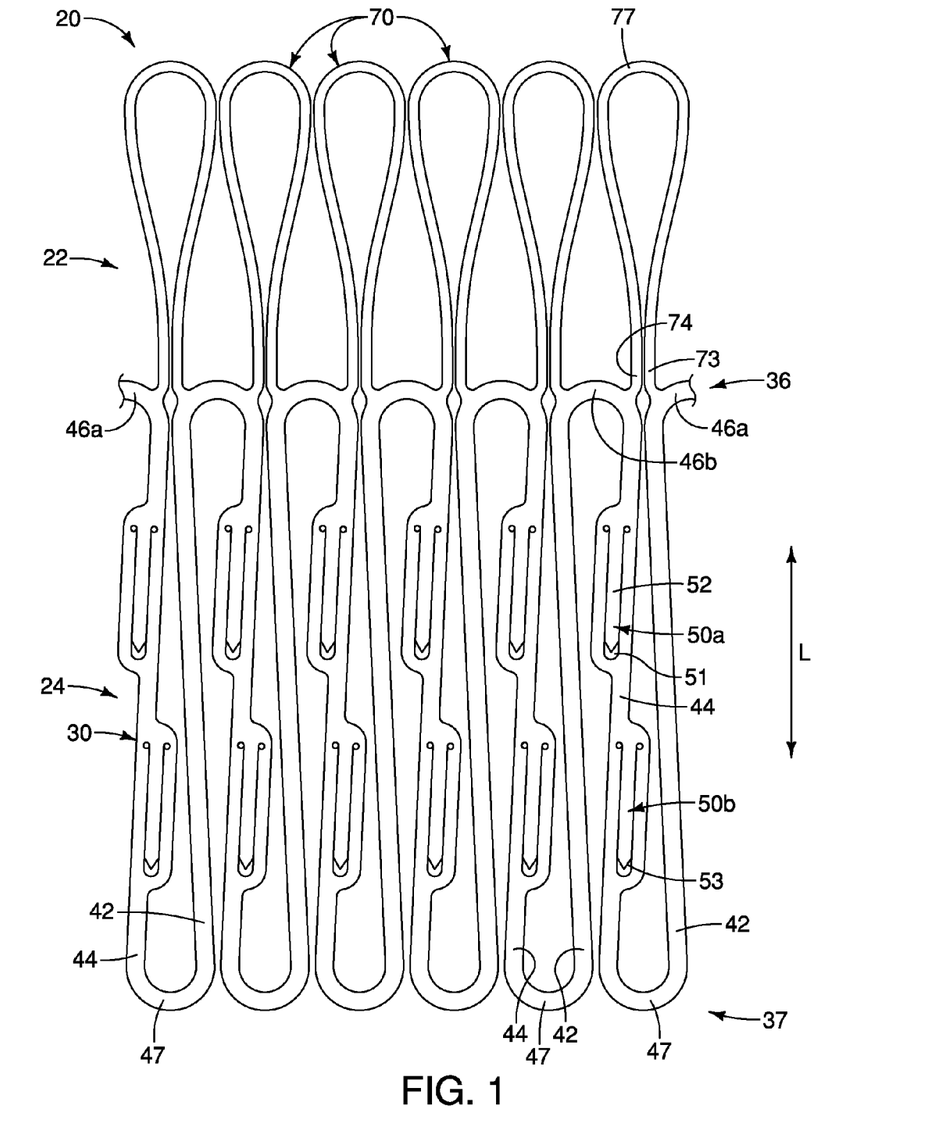
FIG. 1 is a side view of a stent in accordance with one embodiment in a delivery configuration, depicted as flattened for illustrative purposes.
Figure 2:
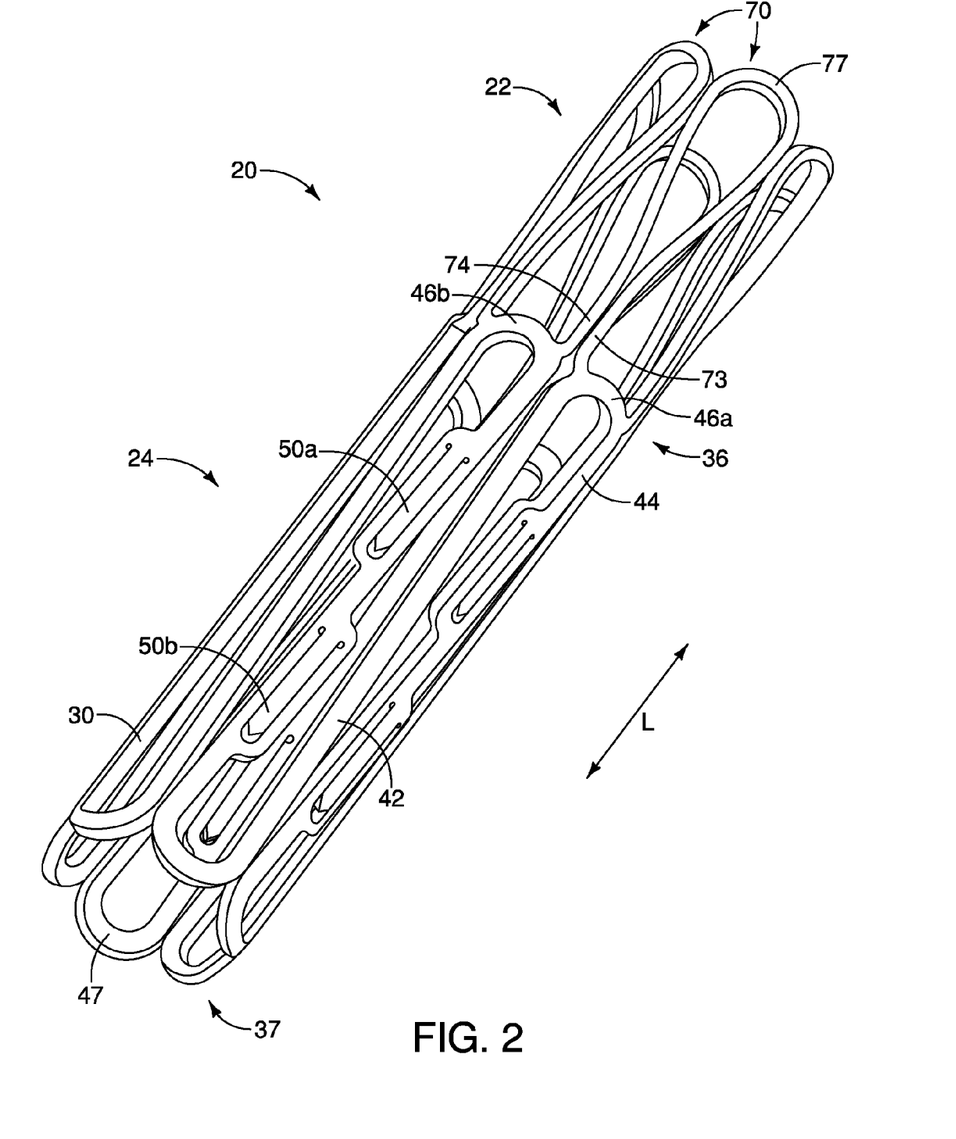
FIG. 2 is a perspective view of the stent of FIG. 1 in a cylindrical, compressed delivery configuration.

Referring to FIGS. 1-2, a stent 20 according to a first embodiment may be manufactured from a continuous cylinder into which a pattern may be cut by a laser or by chemical etching to produce slits in the wall of the cylinder. FIG. 2 shows the cannula-cut pattern of the stent 20 in a compressed, delivery configuration. At least a portion of the cannula-cut structure may then be heat set to give it a desired final expanded, deployed configuration, as generally shown and explained with respect to FIGS. 3-4 below.

Figure 3:
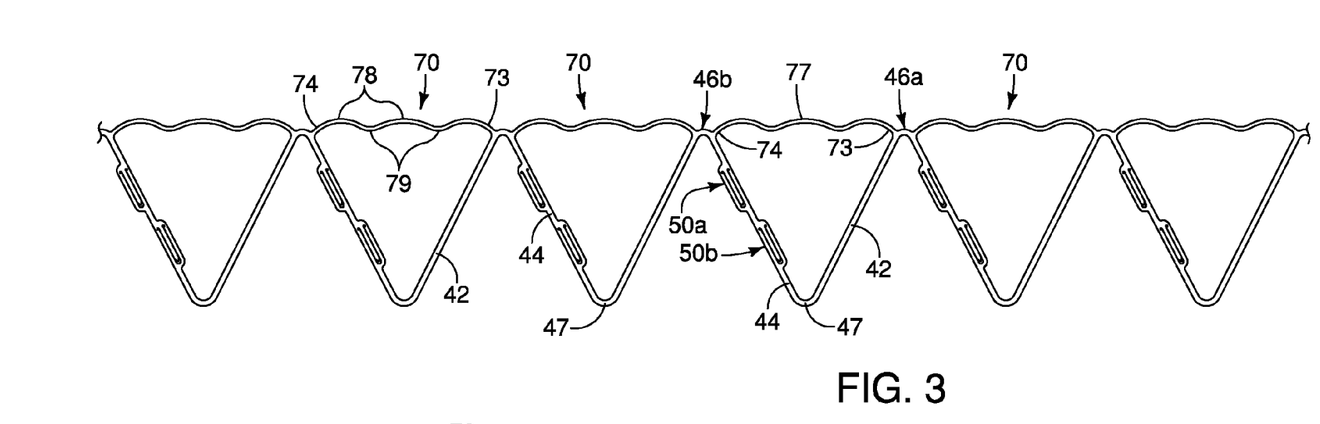
FIG. 3 is a side view of the stent of FIGS. 1-2 in a deployed configuration, depicted as flattened for illustrative purposes.
Figure 4:
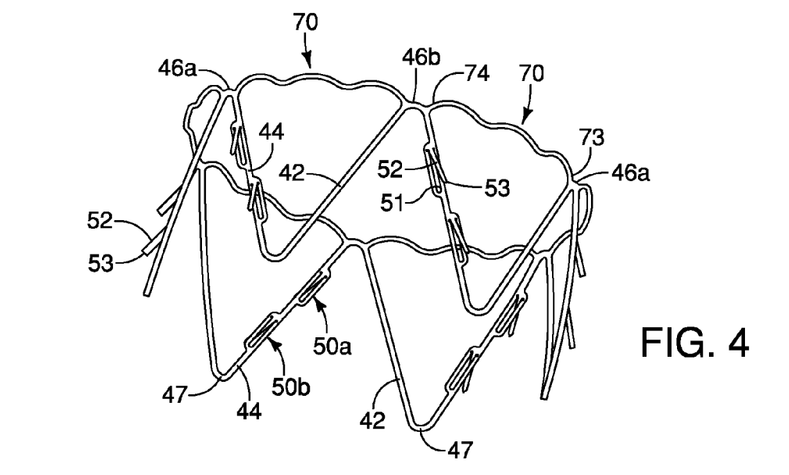
FIG. 4 is a perspective view of the stent of FIGS. 1-2 in a cylindrical, deployed configuration.

The stent 20 preferably comprises two sections, namely a proximal region 22 having one or more proximal conformance struts 70, and a distal region 24 having a main body 30, as shown in FIGS. 1-2. The main body 30 may comprise a generally zig-zag shape in the deployed configuration, having a proximal end 36 and a distal end 37, as shown in FIGS. 3-4 below. The main body 30 may be formed from a continuous main body segment having a plurality of substantially straight first segments 42 and second segments 44. A plurality of proximal apices 46 and distal apices 47 are disposed between the first segments 42 and second segments 44, as shown in FIGS. 1-4.

As will be explained in greater detail in FIGS. 5-6 below, the main body 30 of the stent 20 may be coupled to a graft material 120 to form a stent-graft 110. Accordingly, portions of the main body 30, such as regions of the first and second segments 42 and 44, may be sutured to portions of the graft material 120 using known suturing techniques. The proximal region 22 having one or more proximal conformance struts 70 preferably is not sutured to the graft material 120, for purposed explained in greater detail below.

Referring to FIGS. 1-4, one or more integral barbs 50 may be formed in one or more of the plurality of substantially straight first segments 42 and second segments 44 of the main body 30. The barbs 50 may be formed by laser cutting a desired barb shape into the struts that form the first segments 42 and/or second segments 44. A slit 51 therefore is formed into the struts that form the first segments 42 and/or second segments 44 after the desired barb shape is formed, as shown in FIGS. 1-2. Once the desired barb shape is cut, a main body 52 of the barb 50 may be bent in a radially outward direction with respect to the first segments 42 and/or second segments 44. The angle may comprise any acute angle, as generally shown in FIG. 4 and FIG. 6, or alternatively may be substantially orthogonal or obtuse. If desired, the barbs 50 may be sharpened, for example, by grinding the tip 53 of the barb, to facilitate engagement at a target tissue site.

As shown in FIGS. 1-4, first and second barbs 50a and 50b may be formed in each of the second segments 44 forming the main body 30 of the stent 20. If integrally formed, the barbs 50a and 50b may be formed in areas of the second segments 44 that comprise larger surface areas relative to the first segments 42. Since the portions of the second segments 44 housing the barbs 50a and 50b comprise an increased surface area relative to other regions of the stent 20, it may be easier to perforate portions of the second segments 44 to integrally form the barbs, without adversely affecting the structural integrity of the stent.

While barbs 50a and 50b are shown only on the second segments 44, it will be apparent that one or more barbs may be integrally formed in both the first and second segments 42 and 44. Further, while integral barbs 50a and 50b are shown, the stent 20 may comprise only external barbs that are adhered to a surface of the first segments 42 and/or the second segments 44, or the stent 20 alternatively may comprise a combination of integral barbs and externally adhered barbs.

As noted above, the proximal region 22 of the stent 20 comprises one or more proximal conformance struts 70 disposed between adjacent apices. The proximal conformance struts 70 may be integrally formed with the proximal end 36 of the main body 30, as depicted herein, for example, by way of forming the stent by laser cutting. Alternatively, the proximal conformance struts 70 may be adhered to the proximal end 36 of the main body 30 at one or more locations, for example, using a solder or weld.

The proximal conformance struts 70 comprise a first end 73, a second end 74, and a central region 77 formed therebetween. The first end 73 of each proximal conformance strut 70 may be formed integrally with the main body 30, preferably where one apex 46a of the main body 30 meets a corresponding first segment 42 of the main body, as seen in FIGS. 1-4. The second end 74 of the proximal conformance strut 70 may be formed integrally with the main body 30, preferably near a region where a second proximal apex 46b meets a corresponding second segment 44 of the main body, as shown in FIGS. 1-4. Therefore, in the expanded configuration shown in FIGS. 3-4, each proximal conformance strut 70 may be deployed substantially between a first proximal apex 46a and an adjacent, second proximal apex 46b. As will be set forth in greater detail in FIG. 6 below, the proximal conformance struts 70 may be designed to fill in open spaces between the adjacent proximal apices 46a and 46b to reduce the likelihood of a graft material 120 bowing in a radially inward direction.

Figure 5:
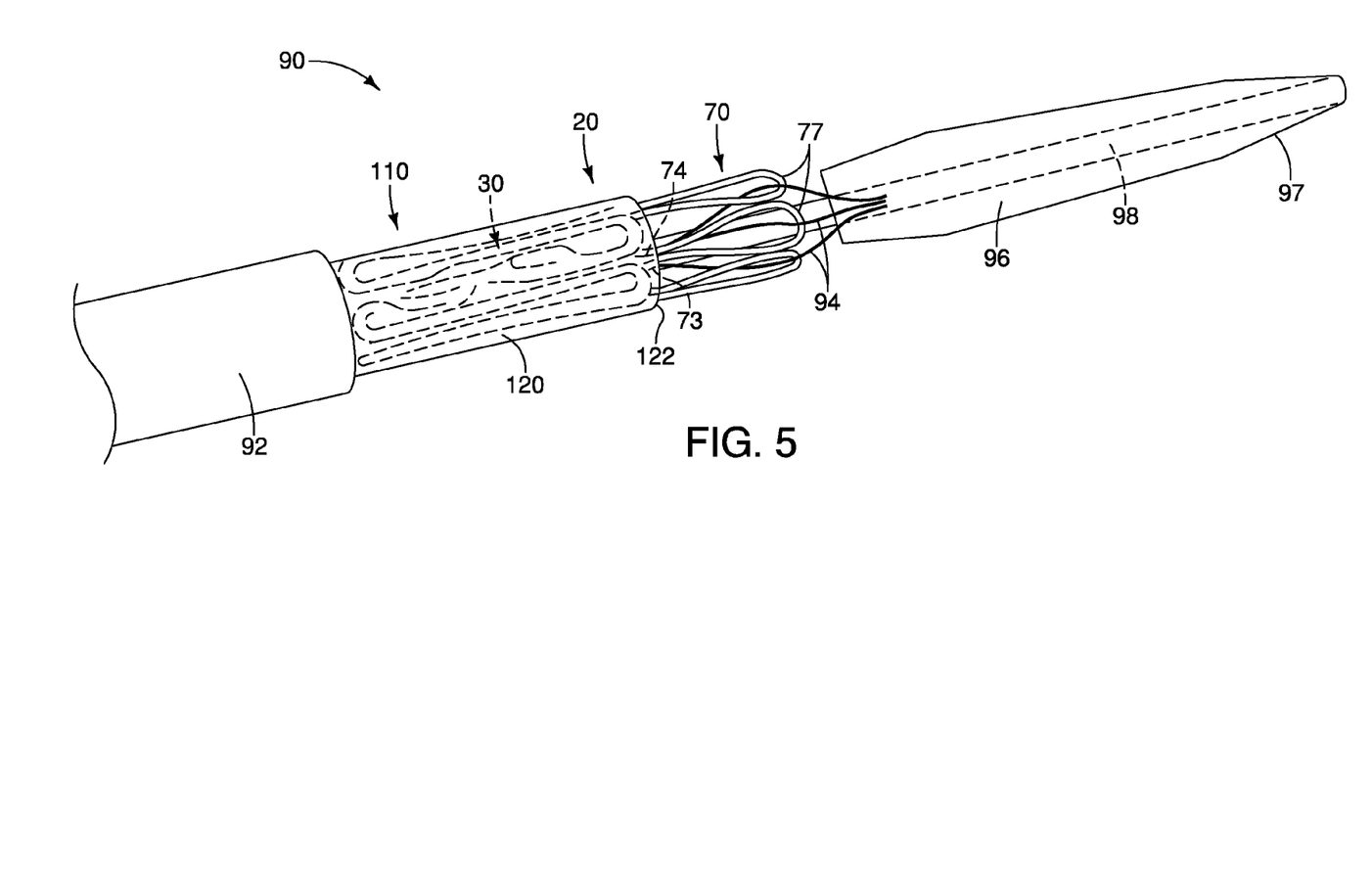
FIG. 5 is a perspective view of an exemplary delivery system that may be used to deliver the stent of FIGS. 1-4, where the stent is coupled to a graft to form a stent-graft.

Referring to the compressed delivery configuration shown in FIGS. 1-2 and FIG. 5, the first end 73 of each proximal conformance strut 70 may extend in a substantially longitudinal direction away from its respective proximal apex 46, i.e., in a direction parallel to a longitudinal axis L of the stent 20, as shown in FIG. 1. Similarly, the second end 74 of each proximal conformance strut 70 may extend in a substantially longitudinal direction away from its respective, proximal apex 46. The central region 77 formed between the first and second ends 73 and 74 of each proximal conformance struts 70 may form a loop or arcuate shape in the compressed delivery configuration, spanning approximately 180 degrees between the first and second ends 73 and 74, as shown in FIGS. 1-2 and FIG. 5.

In accordance with one aspect, the proximal conformance struts 70 do not overlap with the main body 30 of the stent 20 in the compressed delivery configuration, as shown in FIGS. 1-2 and FIG. 5. Accordingly, the stent 20 may be compressed to a relatively small delivery profile, as shown in FIG. 5, and therefore may be delivered into smaller vessels or ducts.

In one embodiment, each proximal conformance strut 70 may be have a depth (e.g., cannula thickness) that is greater than its width (as shown from the side view of FIG. 1). In this embodiment, with such dimensions the moment of inertia may help drive the conformance struts 70 to form the loop or arcuate shape in the compressed delivery configuration, as shown in FIGS. 1-2 and FIG. 5.

The main body 30 and the proximal conformance struts 70 of the stent 20 may be held in the compressed delivery configuration of FIGS. 1-2 using a suitable delivery system 90, as depicted in FIG. 5. In one exemplary embodiment, the delivery system 90 may comprise an outer sheath 92 configured to surround and constrain the stent 20 and the graft material 120 in the delivery configuration. When the constraining outer sheath 92 is removed, the main body 30 and the proximal conformance struts 70 of the stent 20 may assume their respective deployed configurations, as shown in FIGS. 3-4 and FIG. 6. The main body 30 and the proximal conformance struts 70 of the stent 20 may assume their respective deployed configurations either due to the inherent resiliency of the material and/or via heat-set properties of the material. Preferably, at least the proximal conformance struts 70 are heat-set to assume a predetermined deployed configuration upon removal of the outer sheath 92. The main body 30 may be heat-set into the desired zig-zag deployed shape, as shown in FIGS. 3-4 and FIG. 6, or alternatively may assume the zig-zag deployed shape due to the inherent expansile properties of the material forming the main body 30.

Figure 6:
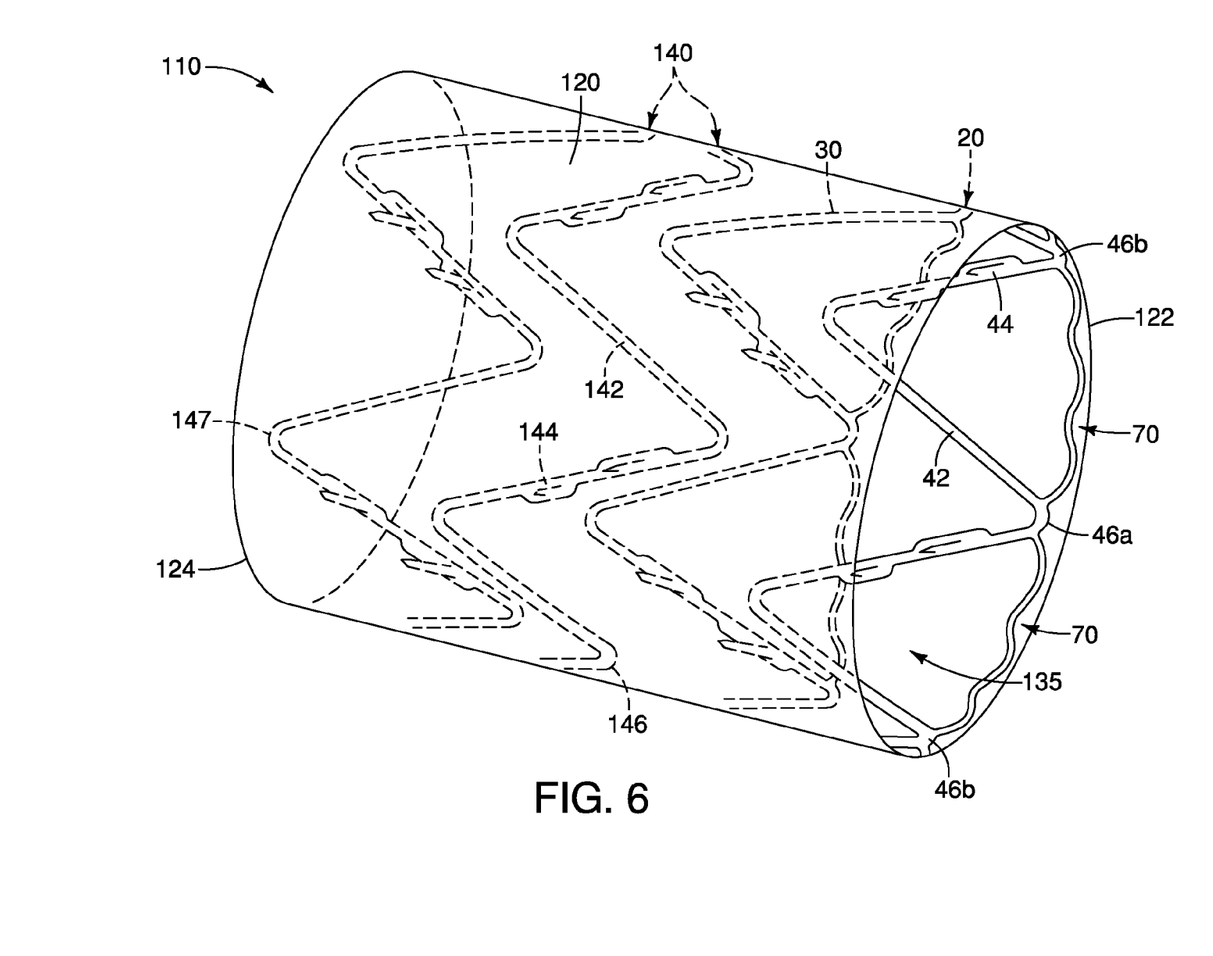
FIG. 6 is a perspective view of the stent of FIGS. 1-4, coupled to a graft to form a stent-graft, in a deployed configuration.

In the expanded deployed configuration, as shown in FIGS. 3-4 and FIG. 6, the stent 20 preferably applies a radially outward force upon at least a portion of a vessel or duct, e.g., to maintain patency within a passageway, or to hold open the lumen of a graft. In the expanded configuration, fluid flow is allowed through a central lumen 135 of the stent 20. It should be noted that the struts of the stent 20 are generally shown having a substantially flat cross-sectional profile, as depicted in FIG. 2 and FIG. 4, but alternatively may comprise a rounded cross-sectional profile or other suitable configuration.

The stent 20 may be manufactured from a super-elastic material. Solely by way of example, the super-elastic material may comprise a shape-memory alloy, such as a nickel titanium alloy (nitinol). If the stent 20 comprises a self-expanding material such as nitinol, the stent may be heat-set into the desired expanded configuration, whereby the stent 20 can assume a relaxed configuration in which it assumes the pre-configured first expanded inner diameter upon application of a certain cold or hot medium. Alternatively, the stent 20 may be made from other metals and alloys that allow the stent 20 to return to its original, expanded configuration upon deployment, without inducing a permanent strain on the material due to compression. Solely by way of example, the stent 20 may comprise other materials such as stainless steel, cobalt-chrome alloys, amorphous metals, tantalum, platinum, gold and titanium. The stent 20 also may be made from non-metallic materials, such as thermoplastics and other polymers.

Figure 7A:
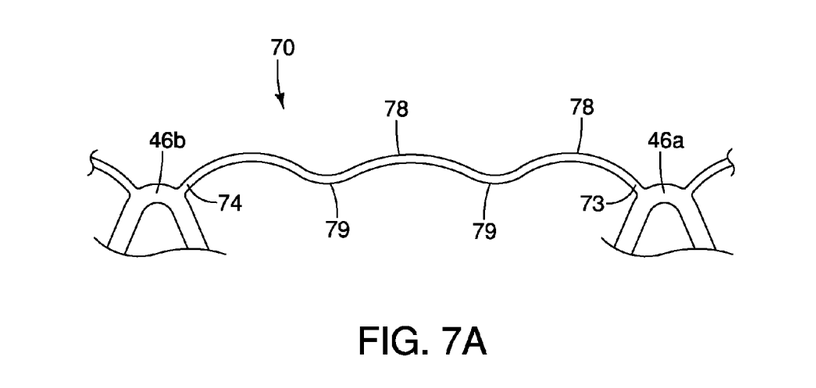
FIGS. 7A-7C are side views depicting alternative deployed configurations of the proximal conformance strut of the stent of FIGS. 1-6.
Figure 7B:
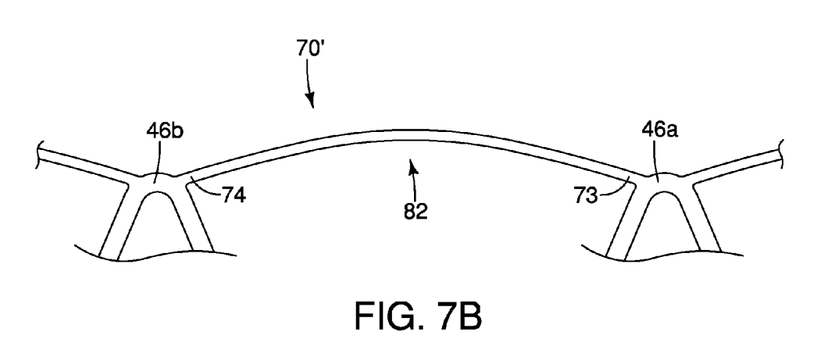
Figure 7C:
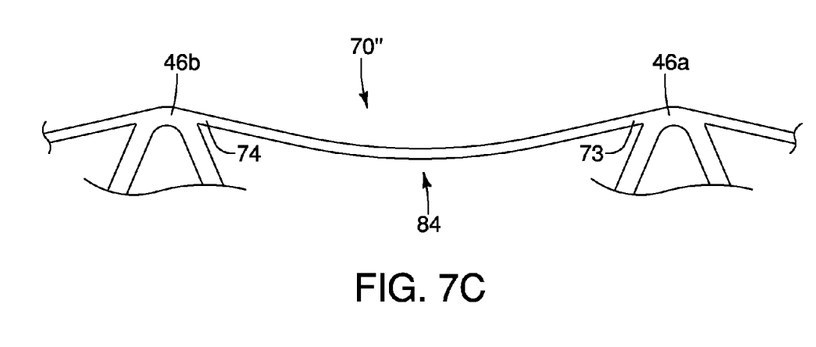

The proximal conformance struts 70 may assume a variety of shapes in the deployed configuration. As shown in FIGS. 3-4 and FIG. 7A, the proximal conformance struts 70 may assume a wave-shaped configuration in the deployed configuration having one or more peaks 78 and valleys 79 formed between the first and second ends 73 and 74. Alternatively, the proximal conformance struts 70 may assume a concave configuration 82 relative to the main body 30, as shown in FIG. 7B, or a convex configuration 84 relative to the main body 30, as shown in FIG. 7C and explained in greater detail below.

In one preferred embodiment, as shown in FIGS. 5-6, the main body 30 of the stent 20 may be coupled to a graft material 120 to form a stent-graft 110. Regions of the first and second segments 42 and 44 may be sutured to portions of the graft material 120 using known suturing techniques. The proximal conformance struts 70, in contrast, are not sutured to the graft material 120. Rather, as shown in FIG. 5, a portion of at least one proximal conformance strut 70 extends proximal to the proximal end 122 of the graft material 120 in the compressed delivery configuration. As noted above, overlap between the main body 30 and the proximal conformance struts 70 therefore is avoided during delivery, allowing for delivery of the stent 20 and associated stent-graft 110 into smaller vessels.

In FIG. 5, the stent 20 and associated stent-graft 110 may be delivered to a target site in the compressed delivery configuration using the delivery system 90 noted above, which may comprise the outer sheath 92, along with one or more trigger wires 94 and a dilator 96. A cannula 98 having a lumen formed therein may be employed and may extend substantially the entire longitudinal length of the delivery system 90. The cannula 98 may be advanced over a previously-placed wire guide, thereby facilitating advancement of the delivery system 90 to a target site.

The exemplary dilator 96 may comprise a main body and a tapered region 97, which facilitates proximal advancement of the delivery system 90 over a wire guide. In particular, a relatively small diameter of the tapered region 97 may allow for atraumatic access and delivery. The one or more trigger wires 94 may be disposed within the confines of the outer sheath 92 and the graft material 120, and may span substantially the entire length of the delivery system 90.

The one or more trigger wires 94 may be used to restrain one or more of the proximal conformance struts 70 during delivery of the stent-graft 110. In one embodiment, a single trigger wire 94 may be looped through selected ones of the proximal conformance struts 70 to restrain the stent 20 during delivery. Preferably, each trigger wire 94 is looped through a corresponding central region 77 of at least one proximal conformance strut 70 to help maintain the proximal end of the stent 30 in a radially compressed configuration. It should be noted that it is not necessary to have an equal number of trigger wires 94 and proximal conformance struts 70, e.g., a trigger wires 94 may only restrain every other proximal conformance strut 70, or an individual trigger wire 94 may be used to restrain multiple adjacent proximal conformance struts 70.

In use, as the stent-graft 120 is delivered towards a target site, the outer sheath 92 preferably is positioned proximally over the entirety of the stent-graft 110, i.e., the outer sheath 92 covers the main body 30 coupled to the graft material 120, and also covers the proximal conformance struts 70. The outer sheath 92 therefore ensures that the entirety of the stent 30 is held in a compressed delivery configuration. When the stent-graft 110 is positioned at a desired location using a suitable imaging technique such as fluoroscopy, a physician may distally retract the outer sheath 92 to expose at least the proximal conformance struts 70. At this time, the proximal conformance struts 70 are still restrained by the one or more trigger wires 94. Therefore, the proximal conformance struts 70 do not expand fully radially outward into engagement with a vessel or duct, and a physician may further tweak or adjust the positioning of the stent-graft 110 relative to the vessel or duct.

When the proper final positioning has been confirmed, the physician may further retract the outer sheath 92, thereby exposing the main body 30 of the stent-graft 110. When no longer radially constrained, the main body 30 of the stent 20 will expand in a radially-outward direction, as shown in FIG. 6. At this time, portions of the graft material 120 may be urged into engagement with an inner wall of a vessel or duct, and may allow flow through the vessel or duct via the central lumen 135.

In a next step, the physician may actuate the one or more trigger wires 94 to release the proximal conformance struts 70, thereby allowing each of the proximal conformance struts 70 to assume the expanded deployed configuration shown in FIG. 6. In the expanded configuration, the proximal conformance struts 70 preferably are aligned inside the proximal end 122 of the graft material 120, as depicted in FIG. 6. When deployed, the proximal conformance struts 70 preferably are disposed substantially perpendicular to the longitudinal axis L and may fill in at least some of the radial spaces between adjacent proximal apices 46a and 46b. Preferably, the proximal conformance struts 70 fill in all of the radial spaces between adjacent proximal apices 46a and 46b and form a circular proximal ring inside the proximal end 122 of the graft material 120, as shown in FIG. 6.

Advantageously, by at least partially encircling the graft material 120 just distal to the proximal end 122 of the graft material 120, the proximal conformance struts 70 may provide enhanced radial support to the graft material 120, which may reduce the likelihood that blood flow may catch on the proximal edge of the graft material. Blood that flows in a distal direction through the stent-graft 110 therefore is less likely to pull the proximal edge 122 of the graft material 120 in a radially inward direction, which may impede blood flow through the central lumen 135 and cause potential endoleaks. Furthermore, the use of a stent 20 as part of a stent-graft 110 may be better suited for use in a curved portion of a vessel, such as the aortic arch or thoracic aorta, where it may be difficult to conform the proximal edge of a stent-graft to the curving vessel wall.

The stent-graft 110 may find particular use in applications where it may not be desirable to have a bare stent segment extending proximal or distal to the graft material 120 in the deployed configuration. As shown in FIG. 6, the entirety of the stent 20 is contained between the proximal and distal ends 122 and 124 of the stent in the deployed configuration.

It will be noted that the stent-graft 110 of FIG. 6 is shown having an additional zig-zag shaped stent 140 disposed distal to the stent 20 described above. The additional stent 140 may be designed similar to the stent 20, with the exception that the conformance struts 70 are omitted, as shown in FIG. 6. The additional stent 140 may be sutured to the graft material 120 at a location distal to the stent 20 and may provide radial support towards the distal end 124 of the graft material 120.

While one additional exemplary zig-zag stent 140 is shown as part of the stent-graft 110 in FIG. 6, the stent-graft 110 may have any number of stents having any variety of shapes, so long as the most proximal stent embodies at least one of the proximal conformance struts 70 described above. In particular, the main body 30 of the proximal-most stent can have struts forming configurations besides zig-zag shapes, and the one or more proximal conformance struts 70 can be used to fill in any open spaces between the struts to help support the graft material 120. Furthermore, while a single proximal conformance strut 70 has been shown between each and every adjacent proximal apex 46a and 46b, one or more proximal conformance struts 70 may be omitted, i.e., there may not be a one-to-one correspondence between the number of proximal conformance struts 70 and proximal apices 46.

In still further applications, distal conformance struts, which may be substantially identical to the proximal conformance struts 70 described herein, may be used to support the distal end 124 of the graft material 120. Such distal conformance struts may be used in lieu of, or in conjunction with, the proximal conformance struts 70 to help prevent the distal end 124 of the graft material 120 from folding inward.

Additionally, it should be noted that the proximal conformance struts 70 preferably are substantially the same radial diameter as the main body 30, when both the main body 30 and the proximal conformance struts are in their respective deployed configurations. In effect, the proximal conformance struts 70 do not substantially bend radially inward or outward relative to the main body 30, and therefore do not substantially urge the graft material 120 inward or outward relative to the proximal apices 46.

Finally, it should be noted that the stent 20 may be used as part of a stent-graft 110, as generally described above, or alternatively may be used as a stand-alone stent to provide support to a vessel or duct without an attached graft material. In the latter embodiment, the stent 20 may be used to treat a wide range of conditions, including but not limited to arterial and biliary stenoses.

Referring to FIGS. 7A-7C, the proximal conformance struts 70 may assume a variety of shapes in the deployed configuration. As shown in FIG. 7A, the proximal conformance struts 70 may assume a wave-shaped configuration in the deployed configuration having one or more peaks 78 and valleys 79 formed between the first and second ends 73 and 74. Alternatively, a proximal conformance struts 70' may assume a concave configuration 82 relative to the main body 30, as shown in FIG. 7B, while a proximal conformance strut 70" may comprise a convex configuration 84 relative to the main body 30, as shown in FIG. 7C.

These proximal conformance strut shapes of FIGS. 7A-7C may be designed to have different advantages. Solely by way of example, the proximal conformance struts 70 of FIG. 7A may provide enhanced rigidity due to the alternating convex and concave portions. As an alternative, the singularly concave-shaped proximal conformance struts 70' of FIG. 7B may help resist inward movement of the distal end 122 of the graft material 120 by extending proximally away from the main body 30. As a further alternative, the singularly convex-shaped proximal conformance struts 70" of FIG. 7C may advantageously help the distal end of the stent 20 better conform to bends in a vessel and provide an enhanced seal. Still further alternative deployed configurations of the proximal conformance struts may be employed are within the scope of the present invention.

Finally, it should be noted that the proximal conformance struts 70 may comprise a reduced profile, including but not limited to width, thickness and/or cross-sectional area, relative to the first and second segments 42 and 44 of the main body 30. For example, as depicted in the figures, the proximal conformance struts 70 generally are narrower in width than the main body 30, which may assist in deployment of the proximal conformance struts 70 from the compressed to expanded configurations. Since a main function of the proximal conformance struts 70 is to resist inward movement of the graft material 120, as opposed to holding open a vessel or duct, the proximal conformance struts 70 can comprise such a reduced profile relative to the main body 30.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A stent-graft for use in a medical procedure, the stent-graft comprising:
   a substantially tubular graft material; and
   at least one stent coupled to the graft material and having compressed and deployed configurations,
   where a proximal end of the stent comprises a plurality of proximal apices at least one conformance strut having a compressed delivery configuration and an expanded deployed configuration, and
   where, in the compressed delivery configuration, the at least one conformance strut comprises a first end and a second end and a proximally extending loop between the first and second ends that is substantially parallel to a longitudinal axis of the stent and extends beyond a proximal end of the graft material, where the first end of the conformance strut is coupled to a first proximal apex of the stent and the second end of the conformance strut is coupled to an adjacent, second proximal apex of the stent wherein the first end of the conformance strut converges with the second end such that the respective ends substantially abut each other at a location proximal of the proximal end of the stent, and
   where, in the deployed configuration, the at least one conformance strut is disposed substantially perpendicular to the longitudinal axis and is aligned inside the proximal end of the graft material.

2. The stent-graft of claim 1 where the at least one conformance strut is integrally formed with the stent.

3. The stent-graft of claim 1 where the stent comprises a zig-zag shape having a plurality of proximal and distal apices, where at least one conformance strut is disposed between adjacent proximal apices.

4. The stent-graft of claim 3 where each proximal apex is connected to the next adjacent proximal apex by a conformance strut to form a proximal conformance ring when the conformance struts are in the deployed configuration.

5. The stent-graft of claim 1 where, in the deployed configuration, the at least one conformance strut is wave-shaped.

6. The stent-graft of claim 1 where, in the deployed configuration, the at least one conformance strut is concave-shaped relative to a main body of the stent.

7. The stent-graft of claim 1 where, in the deployed configuration, the at least one conformance strut is convex-shaped relative to a main body of the stent.

8. The stent-graft of claim 1 wherein the conformance strut further comprises a central region disposed between the first and second ends.

9. The stent-graft of claim 8 further comprising a trigger wire removably engaged with the central region of the conformance strut, the trigger wire configured to restrain the stent in the compressed delivery configuration.

10. A stent for use in a medical procedure, the stent comprising:
    a main body having proximal and distal ends, and further comprising at least one conformance strut coupled to the proximal end of the main body, where the main body and the at least one conformance strut each comprise a compressed delivery configuration and each comprise an expanded deployed configuration,
    where the main body is formed from a single zig-zag stent ring, which in the deployed configuration comprises a plurality of substantially straight first segments and second segments having a plurality of proximal and distal apices disposed therebetween,
    where the at least one conformance strut comprises a first end, a second end, and a central region formed therebetween, where the first end of the conformance strut is coupled to a first proximal apex of the main body, and the second end of the conformance strut is coupled to an adjacent, second proximal apex of the main body, and wherein the first end of the conformance strut converges with the second end of the conformance strut such that the respective first and second ends substantially abut each other at a location proximal of the proximal end of the main body,
    where the at least one conformance strut extends proximal to the proximal apices of the main body in the compressed delivery configuration, and further forms a substantially ring shape together with the proximal apices of the main body in the expanded deployed configuration,
    where the at least one conformance strut comprises a portion having a reduced profile relative to the main body.

11. The stent of claim 10 where the at least one conformance strut is integrally formed with the main body.

12. The stent of claim 10 where the central region of each of the conformance struts comprises an arcuate shape in the compressed delivery configuration.

13. The stent of claim 10 where, in the deployed configuration, the at least one conformance strut is wave-shaped.

14. The stent of claim 10 where, in the deployed configuration, the at least one conformance strut is concave-shaped relative to the main body of the stent.

15. The stent of claim 10 further comprising at least one integral barb formed in at least one of the first and second segments of the main body.

16. The stent of claim 10 where the reduced profile comprises at least one of a reduced width, thickness or cross-sectional area.

17. The stent-graft of claim 10 further comprising a trigger wire removably engaged with the central region of the conformance strut, the trigger wire configured to restrain the stent in the compressed delivery configuration.

* * * * *